United States Patent
Erickson et al.

(10) Patent No.: US 7,318,779 B2
(45) Date of Patent: *Jan. 15, 2008

(54) STATIC POSE FIXTURE

(75) Inventors: Matthew J. Erickson, San Diego, CA (US); Patrick M. Cherveny, San Marcos, CA (US); Adam S. Gile, Oceanside, CA (US)

(73) Assignee: Callaway Golf Company, Carlsbad, CA (US)

( * ) Notice: Subject to any disclaimer, the term of this patent is extended or adjusted under 35 U.S.C. 154(b) by 393 days.

This patent is subject to a terminal disclaimer.

(21) Appl. No.: 11/161,296

(22) Filed: Jul. 28, 2005

(65) Prior Publication Data

US 2005/0255932 A1    Nov. 17, 2005

Related U.S. Application Data

(60) Continuation of application No. 10/708,431, filed on Mar. 3, 2004, now Pat. No. 6,923,731, which is a division of application No. 10/064,739, filed on Aug. 12, 2002, now Pat. No. 6,702,691.

(51) Int. Cl.
*A63B 69/36* (2006.01)

(52) U.S. Cl. .................. 473/266; 473/131; 33/508
(58) Field of Classification Search ............... 473/266
See application file for complete search history.

(56) References Cited

U.S. PATENT DOCUMENTS

| | | | | | |
|---|---|---|---|---|---|
| 4,137,566 | A | * | 1/1979 | Haas et al. ................. | 473/209 |
| 4,694,684 | A | * | 9/1987 | Campbell, III ............. | 73/65.07 |
| 4,891,748 | A | * | 1/1990 | Mann ............................ | 463/1 |
| 5,221,088 | A | * | 6/1993 | McTeigue et al. .......... | 473/201 |
| 5,592,401 | A | * | 1/1997 | Kramer ....................... | 702/153 |
| 5,772,522 | A | * | 6/1998 | Nesbit et al. ................ | 473/222 |
| 5,878,378 | A | * | 3/1999 | Brommer et al. ........... | 702/139 |
| 6,148,280 | A | * | 11/2000 | Kramer ....................... | 702/153 |

* cited by examiner

*Primary Examiner*—Robert E. Pezzuto
*Assistant Examiner*—Joshua P. Wert
(74) *Attorney, Agent, or Firm*—Michael A. Catania; Elaine H. Lo

(57) ABSTRACT

The present invention relates to a static pose fixture (10) used for measuring a subject (42) that is the object of a motion capture system. The static pose fixture (10) provides a means for holding the subject (52) in a static position by using various struts in order to automate the sizing of a computer generated model or to position and orient markers with respect to the model.

2 Claims, 8 Drawing Sheets

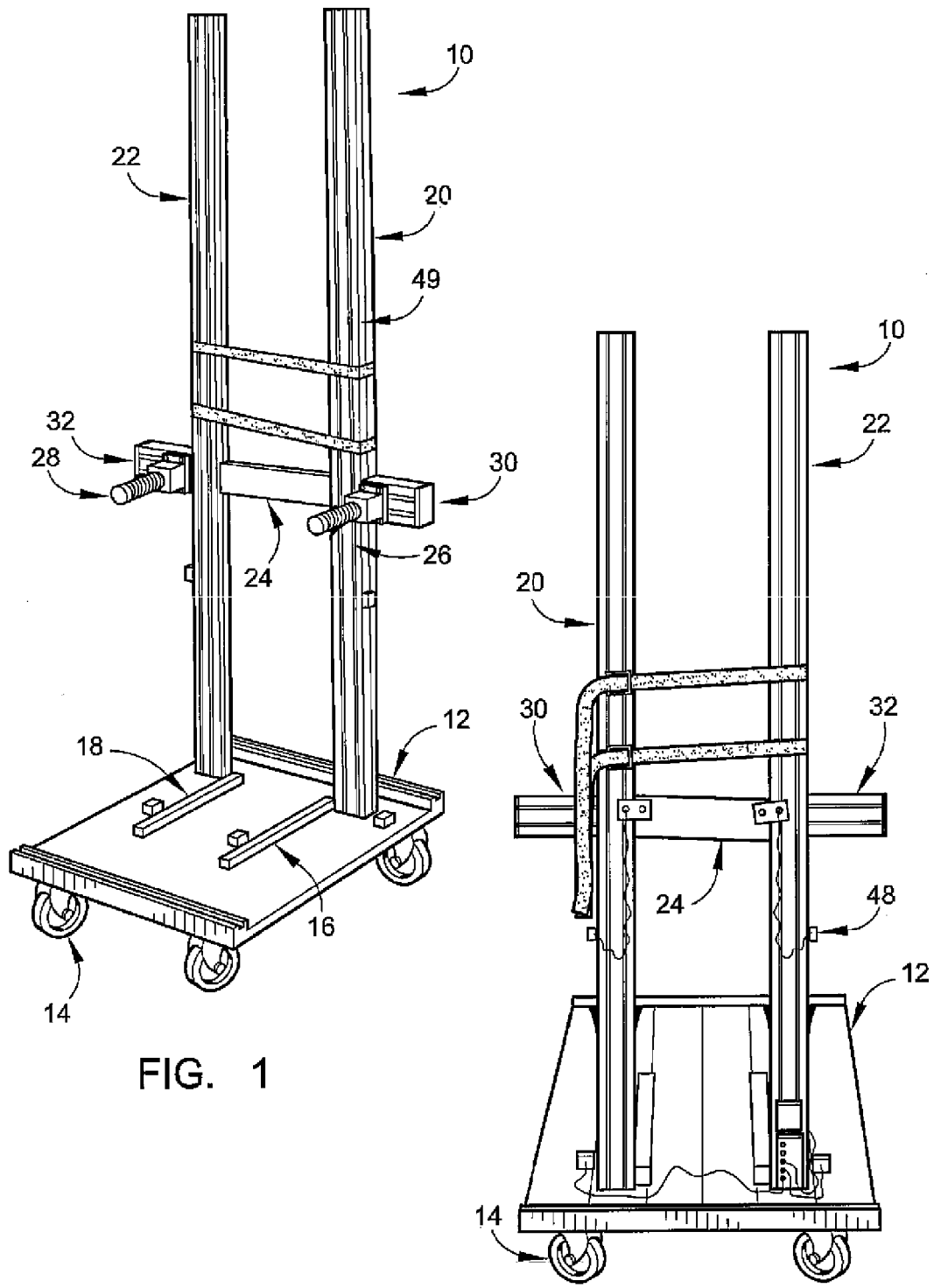

STATIC POSE FIXTURE

CROSS REFERENCES TO RELATED APPLICATIONS

The present application is a continuation application of U.S. patent application Ser. No. 10/708,431 filed on Mar. 3, 2004 now U.S. Pat. No. 6,923,731, which is a divisional application of U.S. patent application Ser. No. 10/064,739, filed on Aug. 12, 2002, now U.S. Pat. No. 6,702,691.

BACKGROUND OF THE INVENTION

1. Field of the Invention

The present invention relates to a static pose fixture that is utilized in motion capture systems. More specifically, the present invention relates to a static pose fixture utilized to measure geometry and body plate marker locations of a subject for preparation of a motion capture model during a golf swing.

2. Description of the Related Art

Motion Capture is used to measure the position and or orientation of any object, usually at multiple points in time. There are four main categories of motion capture devices, mechanical, magnetic, passive optical, and active optical. An example of a mechanical device is the Cyberglove®. A mechanical device measures the orientation of rigid links mounted to a subject. A magnetic device such as the Ascension MotionStar® or Polhemus StarTrak® measures the position and orientation of wire coils attached to the subject. Since golf clubs are typically constructed of metal or metal parts, magnetic systems, which may loose accuracy when metal objects are near by, may experience some distortion during a golf swing motion measurement. Passive optical systems use multiple cameras to triangulate the position of reflective markers placed on the subject. Exemplary examples of a passive optical system are those made by Vicon and Motion Analysis. Active optical systems use triangulation to track the position of infrared light emitting diodes. Exemplary examples of active optical systems include systems such as Northern Digital's Optotrak and Charnwood Dynamics CODA. Active optical systems have the ability to distinguish markers from one another, which greatly decreases the time it takes to process data and which makes them a preferred device for use with the static pose fixture as described herein, however, any of the devices as previously discussed may be used.

An active optical motion device is able to determine the position and orientation of a rigid object as long as 3 non co-linear markers on that object are in view of the sensors. An occluded marker is a marker that is not in view of any of the sensors. One marker on a rigid body plate is selected to be the origin of a coordinate system. The 3D position of each marker on the plate is measured, and the position and orientation of the plate is then reported with respect to the global origin. To generate the best possible motion capture data, it is important to have more than 3 non co-linear markers on each rigid body to increase the chances that at least three markers on the body are not occluded, since the object itself can come between a marker and a sensor.

To drive a computer generated human model with motion capture, data markers of any type (retro-reflective, active IRED, magnetic, etc.), are mounted on the subject in areas where the motion must be acquired. The subject is then asked to stand straight with arms in a horizontal position, thus forming a cross with the body. A frame of data is acquired in the form of a point cloud. Within the software, the operator then moves the human model into the point cloud so that each marker is near the same location within the model as on the subject. If the subject has not assumed the exact same posture as the default posture of the model, the operator rotates the limbs to mimic the subject's posture. If the subject is a different size compared to the model, the operator lengthens or shortens each limb so that it looks correct. Once the model is sized and oriented properly within the point cloud, the configuration is saved and any further motion data acquired from the subject can be used to drive the motion of the model. Some human modeling software allows the user to measure body segments and input values, which can increase accuracy but is relatively time consuming.

Several methods of capturing motion data have been proposed including Nesbit et al., U.S. Pat. No. 5,772,522, which discloses the analysis and measurement of a representative model during an active motion such as a golf swing.

Further examples include Kramer, U.S. Pat. Nos. 5,592,401 and 6,148,280, which disclose the use of sensor devices placed on a subject during an active motion, like a golf swing, thereby enabling the capture and analysis of the motion.

Still more examples include Haas et al., U.S. Pat. No. 4,137,566, which discloses the use of a plurality of reflective sources and a data collector to record active motions, like golf swings, for analysis. Mann, U.S. Pat. No. 4,891,748, discloses using video images in preparation of computer generated models.

However, the process of sizing and orienting the model in the point cloud is time consuming and inaccurate. Because the orientation of each limb in space is estimated by the operator, it is subject to variation and inaccuracy. If it is assumed that the subject is standing with arms perfectly horizontal when the arms are actually skewed slightly or bent, the location of markers on the wrists of the subject will be modeled with a high degree of inaccuracy. As motion capture data is used to drive the model, this inaccuracy will cause the wrist to be driven to a location that is offset from the measured location. When modeling a golf swing, even slight inaccuracy in the wrists can lead to large inaccuracy in the location of the club head, rendering the model far less useful. Additionally, if any of the markers move with respect to the subject once the model generation is complete, the process must be repeated from the beginning or further inaccuracy will result.

BRIEF SUMMARY OF THE INVENTION

The present invention provides a fixture for holding a motion capture subject in a static position in order to automate the measurements of geometry and marker locations. In using motion capture for swing modeling, it is critical to accurately depict the subject that is the object of the motion capture. By using the static pose fixture, the subject is constrained to a static position enabling the pre set body plates to be measured for accurate joint segment length, body angle depiction and body orientation measurements to be used to accurately depict on the model of the motion capture subject.

Furthermore, the present invention enables a technician to make accurate repeatable measurements and eliminates a vast number of steps previously required to perform the measurements and removes variables that typically lead to inaccuracy in designing computer generated models used in motion capture. By identifying and measuring body plate locations of the subject while in the static pose fixture, the static pose fixture also provides a means to automatically position and orient motion agents corresponding to the body plate locations on the model for achieving accurate repeatable subject data.

Moreover, if a body plate moves during the modeling process as often happens, the static pose fixture provides a means to rapidly and automatically re-position the subject's body plate location for measuring segment length, body angle or body orientation, whereas without the static pose fixture, the entire marker orienting process needs to be repeated from the beginning.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 1 is a perspective view of the static pose fixture of the present invention.

FIG. 2 is a back plan view of the static pose fixture of the present invention.

DETAILED DESCRIPTION OF THE INVENTION

Figure 4:
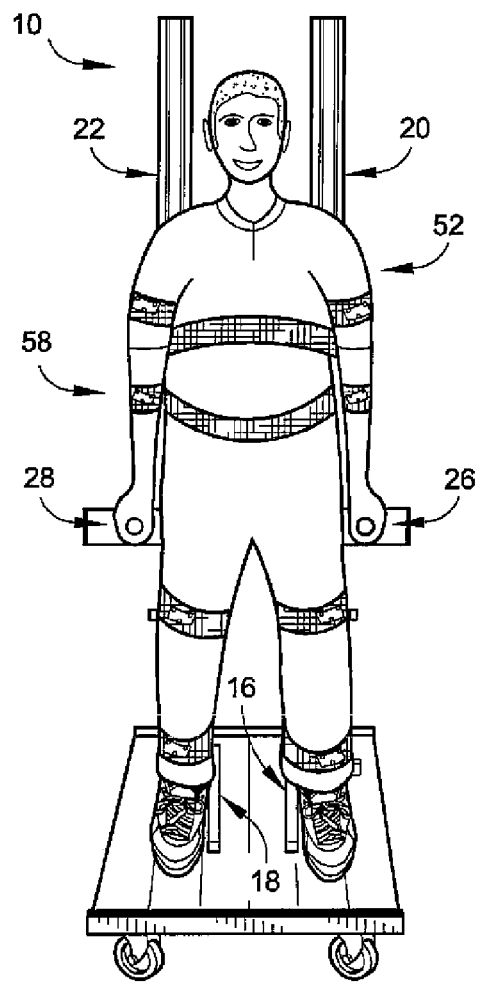
FIG. 4 is a front view of a subject with attached body plates in the static pose fixture.

As illustrated in FIG. 1, a static pose fixture for measuring the size of a motion capture subject 52 is generally designated 10. The static pose fixture 10 of the present invention includes a base 12, first and second foot alignment struts 16 and 18, first and second vertical struts 20 and 22, first and second grips 26 and 28 and first and second slider struts 30 and 32.

The base 12 is preferably substantially flat. The base 12 preferably has a plurality of wheels 14, to provide the fixture 10 with mobility.

Figure 3:
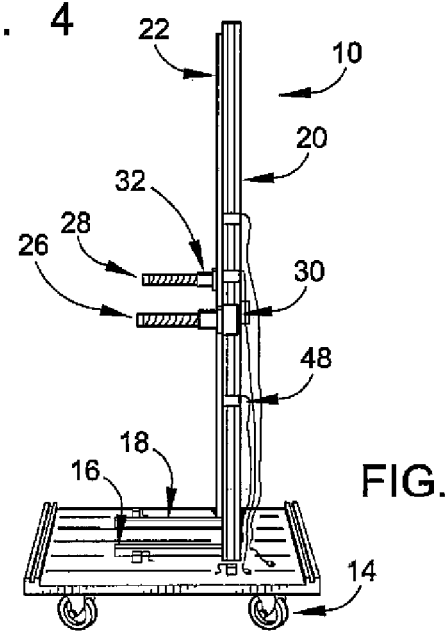
FIG. 3 is a side plan view of the static pose fixture of the present invention.

As illustrated in FIGS. 1-3, first and second foot alignment struts 16 and 18 for placement of a right and left foot of a subject 52 are located on the upper exterior portion of the base 12. The first and second foot alignment struts 16 and 18 are preferably placed at least 4 inches from the rear portion of the base 12. The distance d between the first foot alignment strut 16 and the second foot alignment strut 18 is preferably between 10 inches and 18 inches, more preferably from 10 inches to 14 inches and most preferably 12 inches to allow the feet of the subject 52 to be properly positioned while in the static pose fixture 10. The width of the first and second foot alignment struts 16 and 18 is preferably 1 inch to 3 inches, more preferably 1.5 inches to 2.5 inches and most preferably 2 inches. The first and second foot alignment struts are preferably at least 1 inch in thickness and are attached to the base 12 of the static pose fixture 10 using screws, nut and bolt, or any other well-known means thus enabling adjustment of the first and second foot alignment struts 16 and 18.

Each of a first vertical strut 20 and a second vertical strut 22 are attached to the upper exterior portion of the base 12 at one end of the strut length. The first and second vertical struts 20 and 22 are preferably parallel to each other and placed at least 4 inches from the rear portion of the base. The first and second vertical struts 20 and 22 are attached to the base using a nut and bolt, screw or any other well known fastening means. The vertical struts 20 and 22 are preferably at least 66 inches in length and extend substantially perpendicularly up from the base 12 along the length of the strut. The first vertical strut 20 is located on the outer exterior portion of the first foot alignment strut 16 and the second vertical strut 22 is located on the outer exterior portion of the second foot alignment strut 18. The distance d' between the first and second vertical struts 20 and 22 is at least 12 inches to support the subject 52 in an upright and comfortable position. Additionally, the first and second vertical struts 20 and 22 are preferably between 2 inches and 8 inches in width, more preferably 3 inches to 6 inches and most preferably 4 inches in width to provide structural stability. The first and second vertical struts 20 and 22 are also preferably 1 inch to 4 inches in thickness, more preferably 1 inch to 3 inches and most preferably 2 inches.

A lower back strut, 24 is preferably located at least 30 inches above the upper exterior surface of the base 12 in a horizontal plane between the first and second vertical struts, 20 and 22 to further stabilize the subject 52 while in the static pose fixture 10. The lower back strut 24 should preferably extend at least 15 inches in length for attachment to the first and second vertical struts 20 and 22 at each end and should preferably be at least 2 inches in width and preferably at least 1 inch in thickness to provide support for the back of the subject 52. The lower back strut 24 may optionally include a strap, belt or other device for locking the subject 52 in place during the measurement.

Figure 7:
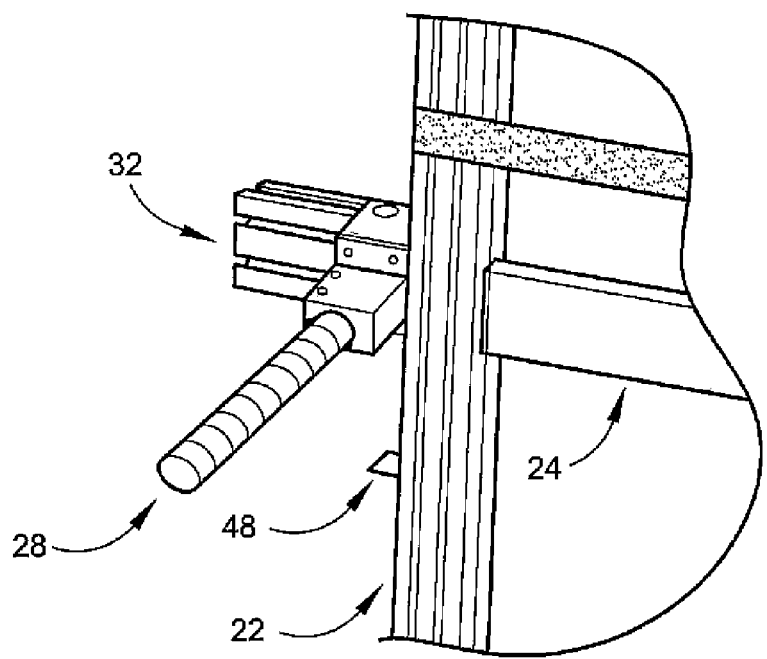
FIG. 7 is an illustrative example of an exemplary grip as used on the static pose fixture.

As illustrated in FIGS. 1 and 7, a first grip 26 is attached to the first vertical strut 20 using a first slider strut 30 on an exterior portion. A second grip 28 is attached to the second vertical strut 22 using a second slider strut 32 along the exterior portion. The first and second grips 26 and 28 are substantially perpendicular to the first and second vertical struts 20 and 22 and substantially parallel to the base 12. The slider struts 30 and 32 permit the first and second grips 26 and 28 to move vertically along the length of the first and second vertical struts 20 and 22. The first and second slider struts 30 and 32, are attached to the first and second vertical struts 20 and 22 with a linear bearing (not shown), however any method that allows the strut to slide up and down may be used including nut and bolt, screw attachment, slide lock and key, bands, pulleys, or levers. The first and second grips 26 and 28 are preferably positioned at least 15 inches above the base 12. The distance between the first and second grips 26 and 28 is between 18 inches and 36 inches, preferably between 20 inches and 32 inches and most preferably between 21 inches and 30 inches. The first and second grips 26 and 28 may be covered to cushion the subject's 52 hands by neoprene, fabric, rubber, foam or other well-known materials to provide cushioning support.

Figure 6:
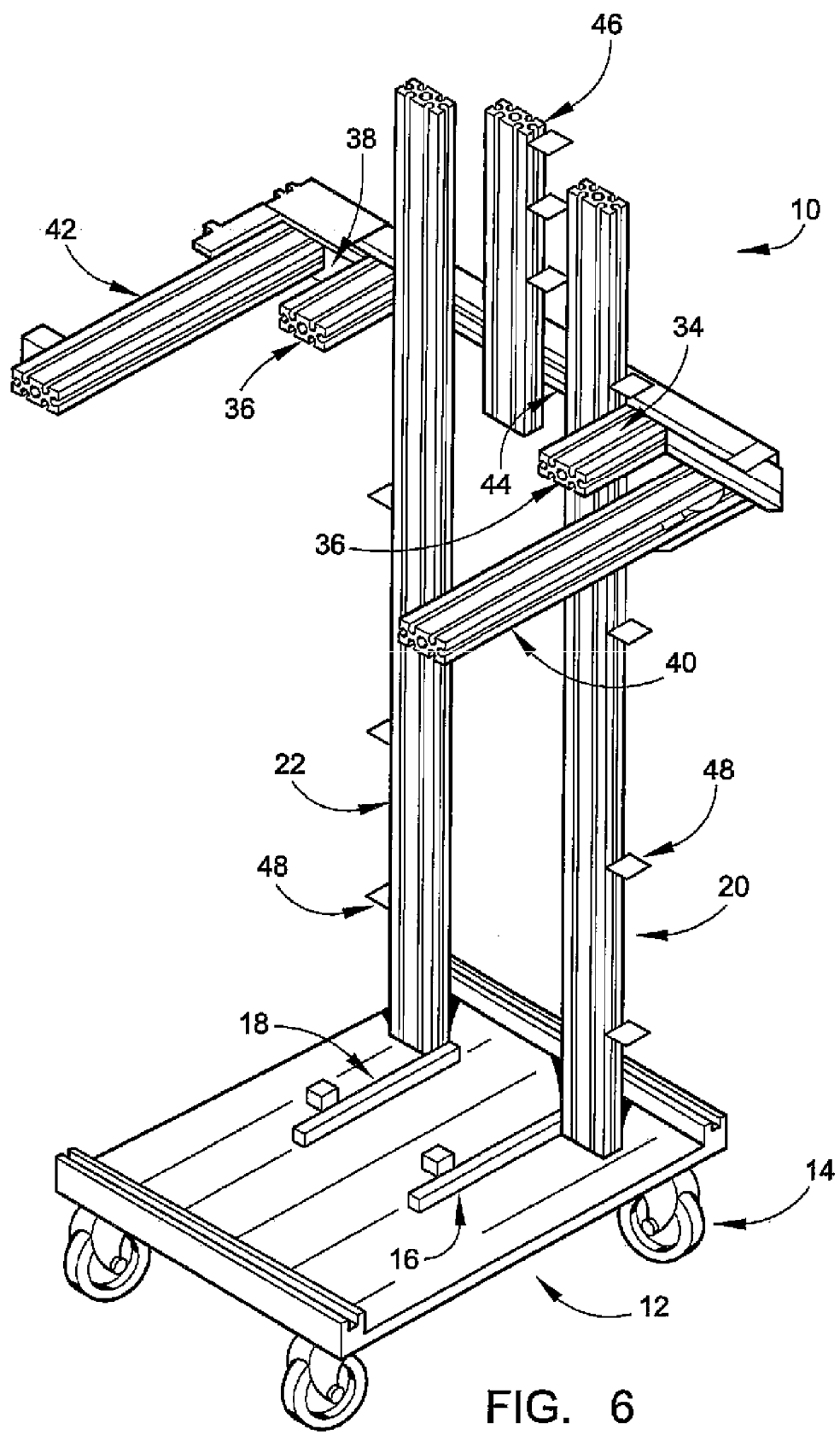
FIG. 6 is a perspective view of an alternative embodiment of the static pose fixture as described herein.

Alternatively, as illustrated in FIG. 6, the static pose fixture 10 has first and second upper arm supports 34 and 36, in place of the first and second grips 26 and 28, thereby supporting the left and right arms of the subject 52 during the measuring process. The first and second upper arm supports 34 and 36 are attached to the rear portion of first and second arm alignment struts 40 and 42. The first and second upper arm supports 34 and 36 are attached to each of the first and second vertical struts 20 and 22 a distance of at least 40 inches from the base 12. The first upper arm support 34 has a right end extending laterally outward from the first vertical strut 20 and the second upper arm support 36 has a left end extending laterally outward from the second vertical strut 22. At least one linear bearing 38 is located on the first and second upper arm supports 34 and 36 to allow the first and second upper arm supports 34 and 36 to move up and down along the length of the first and second vertical strut 20 and 22 to support a subject 52 of any size in the proper orientation. The linear bearing 38 should not allow the first and second upper arm supports 34 and 36 to sag, as the measurements are dependent on the arms being in a parallel 90° angle with respect to the subject's 52 body.

The first arm alignment strut 40 is preferably substantially perpendicular to the first upper arm support 34 at a right end and the second arm alignment strut 42 is preferably substantially perpendicular to the second upper arm support 36 at a left end. The first and second arm alignment struts 40 and 42 are in relation to each other along an elongated strut 44 which is attached to the rear portion of the first and second vertical struts 20 and 22 and also attached to the first and second arm alignment struts 40 and 42 at a right end for the first arm alignment strut 40 and a left end for the second arm alignment strut 42. The elongated strut 44 is preferably located at least 40 inches upward from the base 12 and is preferably at least 18 inches in length. A head and upper back support 46 is attached to the elongated strut 44 at a mid-point. The head and upper back support 46 extends substantially perpendicularly away from the elongated strut 44 to an unattached end. The head and back support 46 is preferably at least 12 inches in length and 3 inches in width to comfortably support the subject's back and head in a steady state position during the measuring process.

The static pose fixture 10 preferably contains at least two sliders 48, located on any of the first and second vertical struts 20 and 22, first and second foot alignment struts 16 and 18, or alternatively on any of the first and second upper arm supports 34 and 36, first and second arm alignment struts 40 and 42, and head and upper back support 46.

Figure 9:
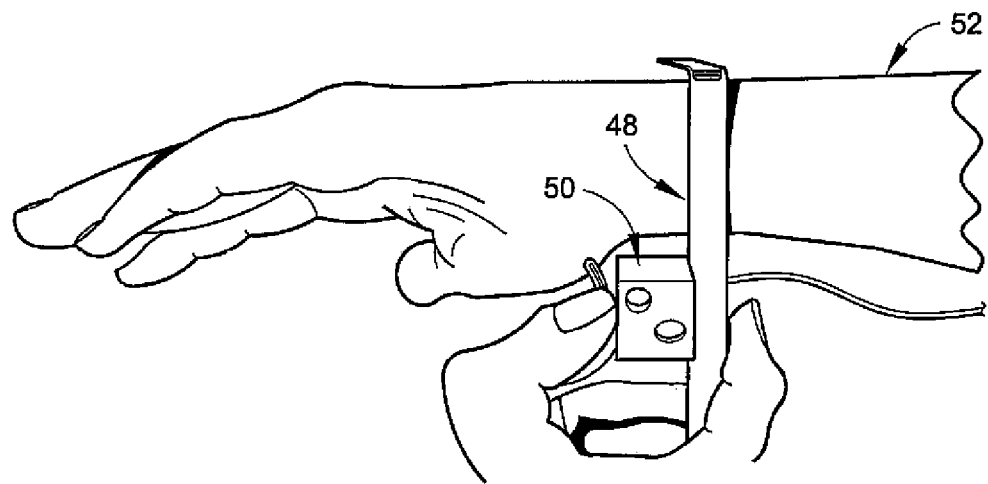
FIG. 9 is an illustrative example of a slider with marker for taking joint center measurements.

As illustrated in FIG. 9, the slider 48, is preferably composed of aluminum, aluminum alloy, composite, steel, or other material. The slider 48 is preferably shaped in a rectangular or block formation, however it is not limited to this formation. The slider 48 contains at least one reflective means 50 bonded to it. The reflective means 50 is preferably bonded to the slider 48 using epoxy, solder, or other well-known means. The slider 48 moves freely along the length of the strut along grooves 49 located in the strut length. The slider 48 is adjusted along the length of the strut using a nut and bold, hex and key or any other well-known means. One slider 48 is preferably aligned with a major joint segment of a subject's 52 body, while another slider 48 is aligned with a different joint segment of the subject's body thereby increasing the accuracy of determining the length between the subject's 52 limbs by calculating the distance between two sliders 48.

The static pose fixture 10 is preferably constructed of aluminum, aluminum alloy, steel, or other material providing the requisite sturdiness to support the subject 52 during the modeling process. Extruded aluminum is most preferable as it provides the optimum weight and durability required.

Figure 8:
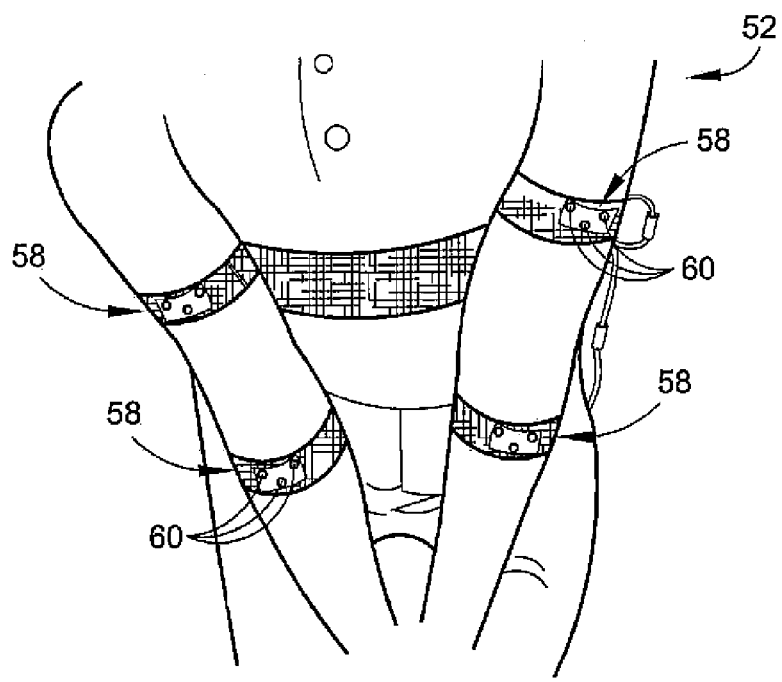
FIG. 8 is an illustrative example of a body plate with marker for measuring the position and orientation of the subject's limbs while in the static pose fixture.

As illustrated in FIG. 8, to optimize motion capture modeling using the static pose fixture 10, a subject 52 is placed in a marker interface suit. This step involves attaching at least one body plate 58 to the subject 52 at various joint locations. The body plate is preferably attached to the subject 52 using clamps, elastic bands, straps, clasps, hook and loop closures or any other well-known means. A preferred method involves wrapping lengths of stretch fabric around each limb of the subject 52. An exemplary stretch fabric for this purpose is Velstretch®. Subsequently, at least one body plate 58 is attached to the stretch fabric using epoxy, snaps, velcro, or any other suitable means of attachment. The body plate 58 may also optionally be cushioned against the subject's 52 limbs by attaching or placing rubber, foam, cloth, or any other material that provides cushioning effect to or between the body plate 58 and the subject's 52 limb.

The body plate 58 is preferably composed of rubber, plastic, composite or ceramic, as shown in FIG. 8, the body plate 58 of the present invention is preferably composed of a composite material. The composite material reduces the mass of the body plate 58, while providing a stable base for mounting on the subject. Additionally, the composite material is preferably molded to provide a curved body plate 58 permitting better positioning of the body plate 58 on the subject's 52 limbs. It is preferable to use curved body plates 58 for this purpose, however the body plates 58 are not limited to a curved configuration. The body plate 58 preferably ranges from 0.50 inch to 3.0 inches in width, 2.0 inches to 9.0 inches in length and 0.10 inch to 1.0 inch in height. The body plate 58 also preferably contains at least three markers 60*a-c*, but may contain as many as 15-20 markers for measuring the location of the body plate 58 on the subject 52. These markers 60*a-c* are preferably retro-reflective, active IRED, or magnetic, but are not limited to these types. As illustrated in FIG. 8, one marker 60 in a body plate 58 is selected to be the origin of a localized coordinate system. The 3D position of each marker 60 on the body plate 58 is measured, and the position and orientation of the body plate 58 is then reported with respect to a global origin. Additionally, at least one marker 60 is located on the base 12 of the static pose fixture 10 to act as an origin point for the localized coordinate system in the event that one of the markers 60 on the body plate 58 is obscured. The body plate 58 is then connected to a strobe box (not shown), which controls the marker 60 illumination. The use of a curved body plate 58 in conjunction with at least three markers 60*a-c* on the body plate 58 alleviates the event of complete marker occlusion thus insuring that at least one body plate marker 60 will be visible.

Once the body plate 58 has been attached to the subject 52, the body plate 58 locations are then optimized on the subject 52. With a motion capture system active, the subject 52 swings a golf club 62 and the data quality is evaluated by examining a chart of missing data. If less than three body plate markers 60a-c on a body plate 58 are in view, the system will generate no data for the body plate 58 at that instant. It is important that fast moving body plates 58 such as those on the arms are not occluded for more than 3 consecutive frames during the downswing or accuracy will be lost when the missing data is interpolated. If this occurs, body plates 58 that are occluded excessively are preferably moved slightly, the subject 52 then swings again, and the data quality is evaluated. This process is repeated until body plate 58 locations have been optimized.

Figure 5:
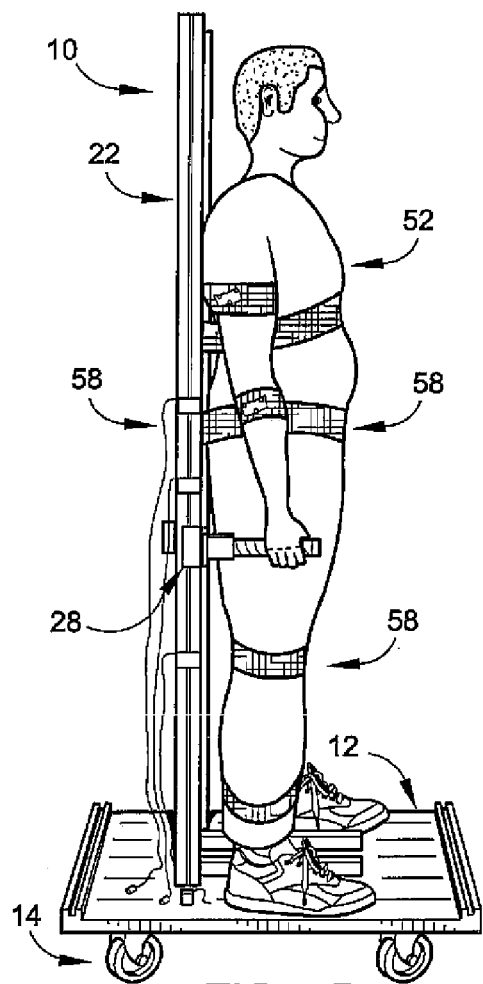
FIG. 5 is a side view of a subject with body plates attached in the static pose fixture.

As illustrated in FIGS. 4 and 5, once the body plate 58 locations have been optimized, the subject 52 is then placed in the static pose fixture 10. The subject 52 is constrained to a static position and orientation for measurement of the geometry and marker location.

Figure 10:
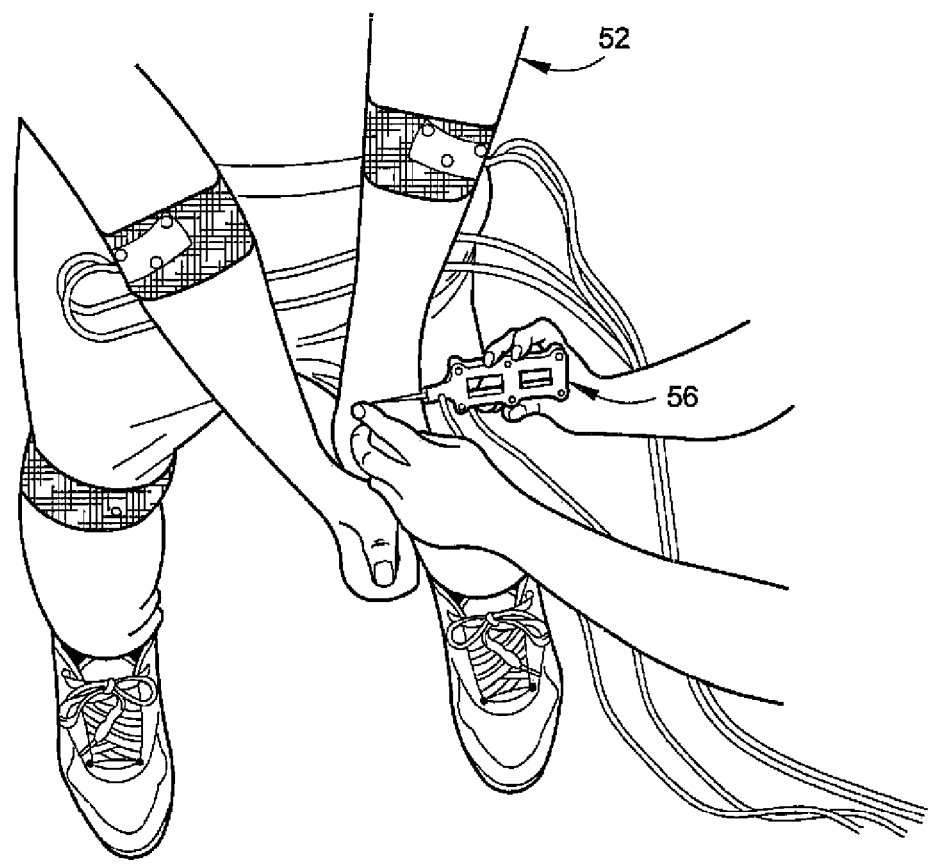
FIG. 10 is an illustrative example of a joint center measurement taken using a digitizing probe.

Joint center measurements are preferably obtained while the subject 52 is in the static pose fixture 10 by using a digitizing probe 56 as illustrated in FIG. 10. By having the subject's 52 arms point down and the hands wrap around the first and second grips 26 and 28 near the subject's 52 hips. A digitizing probe 56 is preferably used to measure the distance between various joint segment lengths including the subject's wrist joints, which are often difficult to measure. An exemplary digitizing probe is manufactured by Northern Digital, which measures the position of the probe tip with respect to a selected object. The probe 56 is preferably used to mark at least four locations on a subject's 52 body thereby recording the position and orientation of various joint segments on the subject's 52 body with respect to position, providing positional coordinates and angularity, which is preferably used to set a coordinate system with respect to the global origin. A computer program calculates the length and orientation of each body segment from the digitizing probe measurements, to build the computer model 64 of the subject 52. Additionally, for more precise measurements while the subject 52 is in the static pose fixture 10, the position and orientation of each of the rigid body plates 58 on the subject 52 is preferably measured and recorded.

Alternatively, joint center measurements are obtained when the arms are positioned shoulder height and the elbows are bent at 90° degree angles away from the body. The linear bearing 38 on the first and second arm alignment struts 40 and 42 are raised or lowered so that the arms rest horizontally. The linear bearing 38 on the first and second arm alignment struts 40 and 42 nearest the elbows of the subject 52 are then moved toward or away from the shoulders so that the elbows rest against the first and second arm alignment struts 40 and 42. A slider 48 with at least one means 50 bonded to it is then placed on the first and second arm alignment struts 40 and 42 corresponding to each major joint center on the subject's 52 arms. A slider 48 is also placed on the first and second vertical struts 20 and 22, first and second foot alignment struts 16 and 18, first and second arm supports 34 and 36 and head and upper back support 46. The slider 48 is adjusted to align with the appropriate joint center and locked in place. A motion capture system is then used to measure the 3D coordinates of the sliders 48, as well as the position and orientation of each of the rigid body plates 58 mounted to the subject 52. The distance between two sliders 48, such as those aligned with the wrist and elbow is calculated and the result is the length of the corresponding limb, in this case, the forearm. The length of each limb is determined by the computer, which calculates the distance between sliders 48. These lengths are then used to properly size segment lengths in the computer generated player model 64. The body plate 58 position and orientation data is used later to locate the motion agents on the swing model 64 and the measurements are later run into a computer program that calculates the length and orientation of each body segment, to build the computer model 64 of the subject 52. A model 64 is preferably built with limb lengths based on the slider 48 measurements and limb orientations assumed to be either 0° or 90°. Furthermore, using the rigid body plate 58 measurements obtained while in the static pose fixture 10, each of the limbs and limb angles will be in the correct position and orientation for the motion capture program.

Once the measurements have been determined, swing motion is preferably captured using a motion capture system and any experiment involving measuring the swing motion of a player. If at any time the body plates 58 move on the subject's 52 body, the subject 52 can re-enter the static pose fixture 10 and a new frame of data is preferably collected. The use of the static pose fixture 10 makes resetting the body plate 58 locations less time consuming and more accurate then was previously available by allowing the subject 52 merely to re-enter the static pose fixture 10, re-set in the known position and realign the body plates 58. Additionally, the slider 48, which has already been locked in place for the subject 52, is preferably used to re-align the subject 52 according to the pre-set slider 48 positions.

Figure 11:
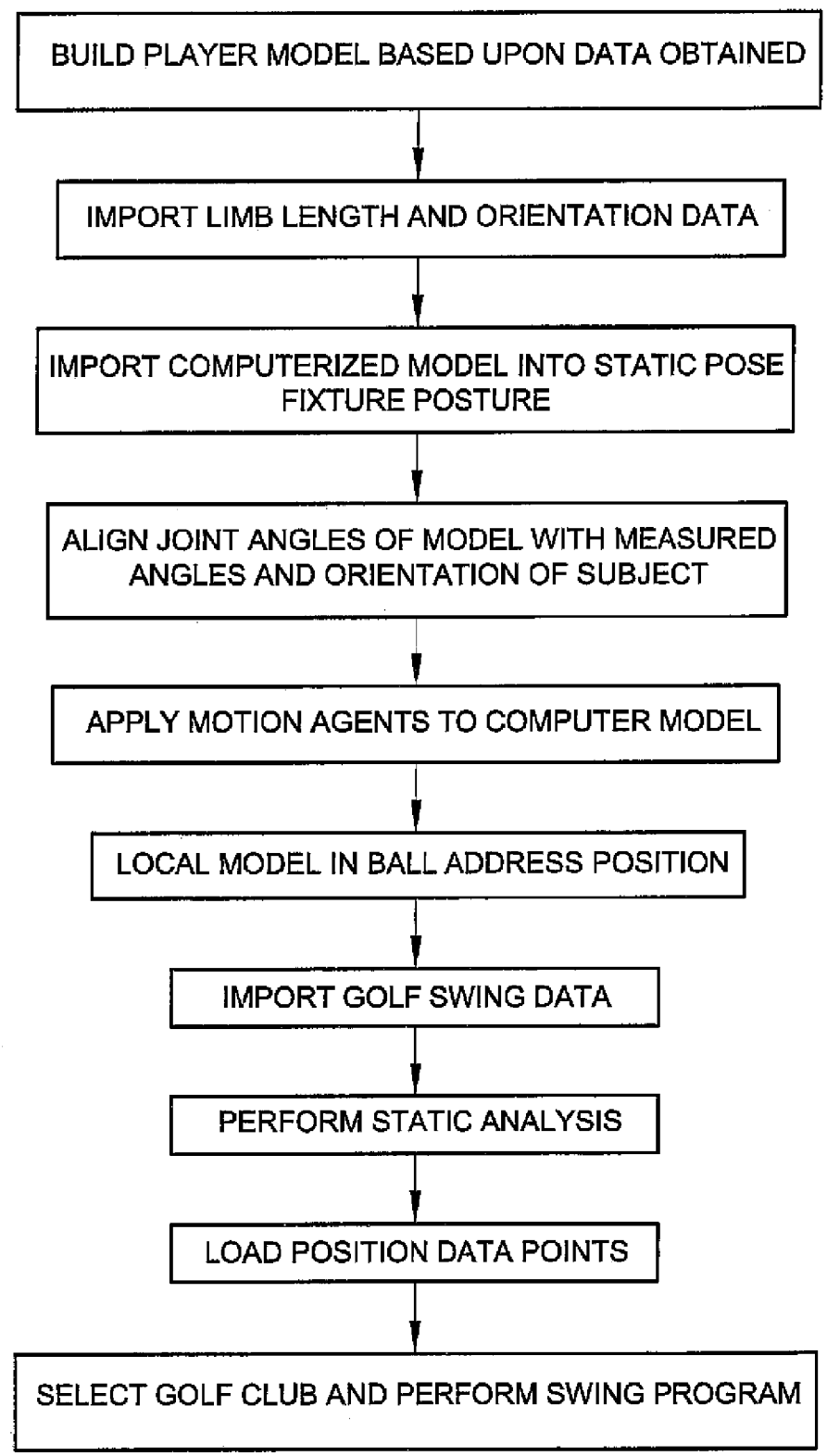
FIG. 11 is a graph of the computer modeling process using the static pose fixture as described.

As illustrated in the graph of FIG. 11, during the capture of swing data, each swing is post-processed using computer programming software that fits plate position and orientation with a polynomial curve in order to fill in any gaps in data that is missing due to an occluded marker 60. An exemplary computer programming software package for data is MATLAB® software.

Next, a player model 64 is built using the measurement data obtained while the subject 52 was constrained in the static pose fixture 10. Various computer software packages are preferably used to build a player model 64; one exemplary program is the ADAMS FIGMOD® software package. To build a player model 64, the height, weight and age of the subject 52 is entered. The software uses this information to build a player model 64 with average mass properties based on an anthropomorphic database.

Next a file with the limb length and orientation data and body plate 58 position and orientation data previously collected is imported. The software uses the limb length data to automatically size each of the model's 64 limbs.

Next the computerized player model 64 is brought into the static pose fixture 10 posture. In this step, each of the model's 64 joint angles is adjusted to the same angles that were measured on the subject 52 while in the Static Pose Fixture 10. Each limb of the model 64 now occupies the same space in the model 64 coordinate system as it did in the measurement coordinate system.

Figures 12, 13:
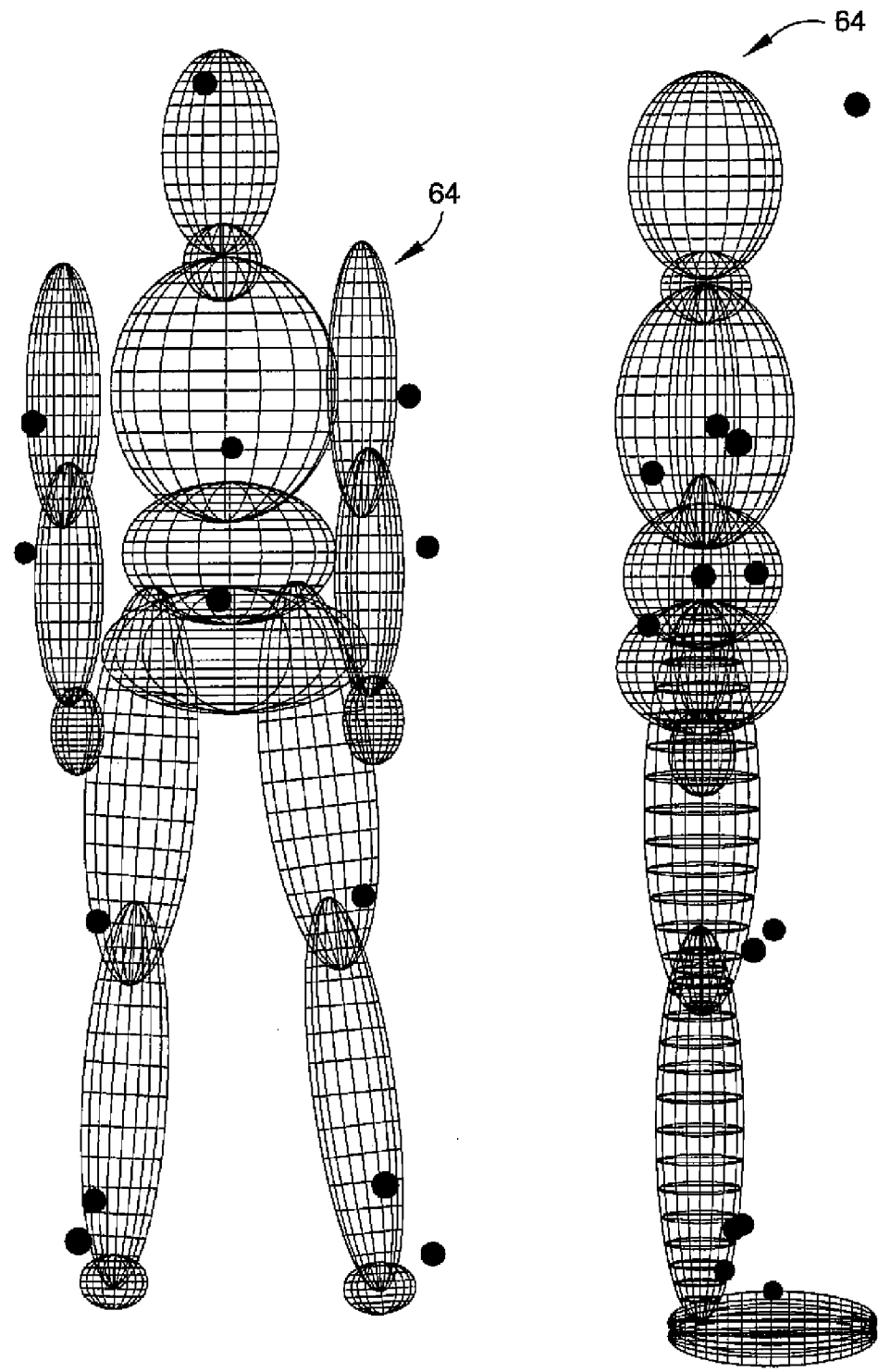
FIG. 12 is a front view of a computer generated model in the static pose posture with motion agents applied.
FIG. 13 is a side view of a computer generated model in the static pose posture with motion agents applied.

As illustrated in FIGS. 12 and 13, motion agents are applied to the model 64 while in the static pose posture. Illustrative spheres representing origins of each of the rigid body plates 58 are linked to each limb of the model 64 as measured using the static pose fixture 10. Later, minimizing the distances and angles between the data points and the motion agents will control the model's 64 motion. With the model 64 correctly sized and oriented in previous steps, motion agents are simply loaded into space in the position and orientation measured while the player was in the static pose fixture 10. Each agent is then rigidly linked to its corresponding limb.

Figure 14:
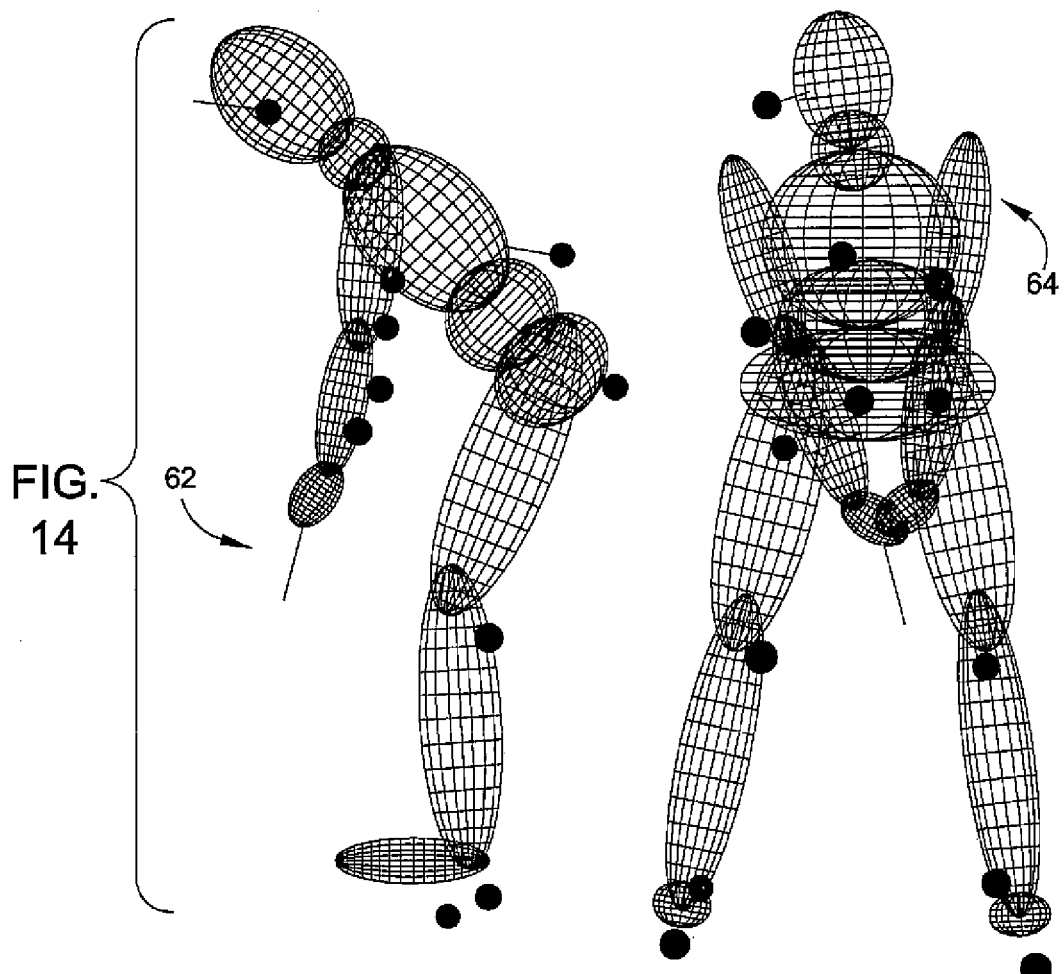
FIG. 14 is a view of a computer generated model in ball address position as modeled using the static pose fixture.

The joint angles and limbs as defined by the body plate 58 locations of the player model 64 are rotated to bring the player into a pose that is similar to a typical ball address position as illustrated in FIG. 14. This will make it easier for the software to bring the player into the measured address position later.

Previously collected swing data is then imported and the first frame of data with the player in the address position is loaded into the software program.

Once the swing data is set, the computer program performs a static analysis to minimize the distance between the motion agents and the data points in the first frame of data. This brings the player model 64 into the measured address position.

Additionally, position data points obtained using the digital probe 56 are preferably loaded into the program. These points will show up in space in the same location as previously measured. Points on the axes of the model's 64 joint segments are moved to the measured joint segment points and locked in those locations. In addition, difficult to measure wrist data is incorporated into the program through measurements obtained using the digital probe.

A club 62 is preferably selected for the player model 64 and a parametric model of the golf club 62 can be loaded and gripped by the player model 64. The selection of a particular club 62 allows the affects that various club properties have on a player's swing to be evaluated as well as the performance of various products for a particular swing.

Figure 15:
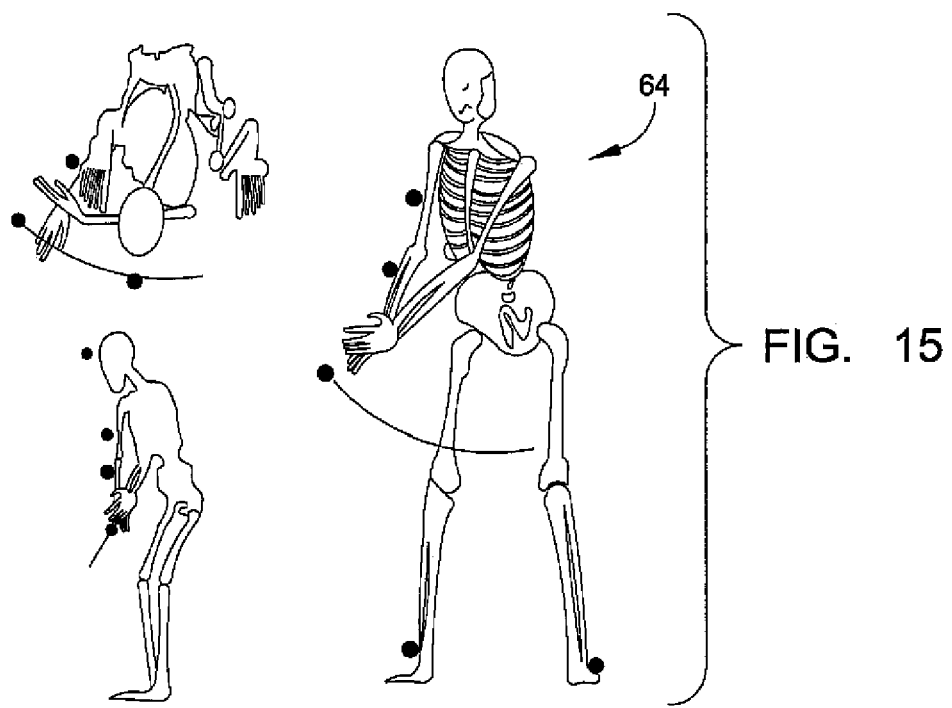
FIG. 15 is an example of a computer generated model stepping through swing data generated by the computer program using the measurements established while in the static pose fixture and club selection data.

Once the club 62 has been selected and assigned to the player model 64, the swing model is actuated. The player model 64 is preferably shown as a computer-generated model 64 or in a more animated form as illustrated in FIG. 15. The swing model allows the program to step through the swing data frame by frame and maintain the minimum distance between the data points and motion agents. Effectively, this step causes the model 64 to reproduce the actual swing with a high degree of accuracy.

Additionally, joint torque values are determined using inverse dynamics, as performed in the ADAMS FIGMOD® program to calculates the torque produced by each joint throughout the swing based on the swing motion and mass and size properties of the player's limbs. Once the joint torque values are assigned, the model 64 applies the joint torque values to the player model 64 through time, rather than minimizing the distance between motion agents and data points. In this mode, club properties can be varied, and the affects of these variables on swing motion can be studied.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes, modifications and substitutions of equivalents is preferably made therein without departing from the spirit and scope of this invention which is intended to be unlimited by the foregoing except as may appear in the following appended claims. Therefore, the embodiments of the invention in which an exclusive property or privilege is claimed are defined in the following appended claims.

What is claimed is:

1. A system for measuring a person who is a subject of a motion capture model, the system comprising:
   a static pose fixture comprising
      a base having a substantially flat surface,
      a pair of foot alignment struts located on the upper rear surface of the base wherein the distance between a first foot alignment strut and a second foot alignment strut is at least 10.0 inches,
      a pair of vertical struts located on the upper rear surface of the base wherein a first vertical strut is located on an outer exterior portion of the first foot alignment strut and a second vertical strut is located on an outer exterior portion of the second foot alignment strut, and
      a pair of grips attached to the pair of vertical struts and located at least 15 inches above the base;
   a plurality of markers positioned on the person;
   means for recording the position and orientation of each of the plurality of markers positioned on the person;
   means for measuring the subject to generate a plurality of measurements;
   means for converting the measurements into a localized coordinate system; and
   means for generating a computer model of the subject based on the measurements.

2. A method of measuring a subject which is an object of a motion capture model, the method comprising:
   attaching at least one body plate to the subject;
   optimizing a location of the at least one body plate;
   positioning the subject in a static pose within a static pose fixture comprising
      a base having a substantially flat surface,
      a pair of foot alignment struts located on the upper rear surface of the base wherein the distance between a first foot alignment strut and a second foot alignment strut is at least 10.0 inches,
      a pair of vertical struts located on the upper rear surface of the base wherein a first vertical strut is located on an outer exterior portion of the first foot alignment strut and a second vertical strut is located on an outer exterior portion of the second foot alignment strut, and
      a pair of grips attached to the pair of vertical struts and located at least 15 inches above the base;
   measuring at least two joint segment lengths of the subject;
   converting the measurements of the two joint segment lengths into a localized coordinate system; and
   generating a computer model of the subject based on the measurements of the two joint segment lengths.

* * * * *